United States Patent
Berger

(10) Patent No.: US 10,460,904 B2
(45) Date of Patent: Oct. 29, 2019

(54) IMAGING DEVICE FOR IMAGING AN OBJECT AND FOR IMAGING A STRUCTURAL UNIT IN A PARTICLE BEAM APPARATUS

(71) Applicant: Carl Zeiss Microscopy GmbH, Jena (DE)

(72) Inventor: Wolfgang Berger, Gerstetten (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 15/886,269

(22) Filed: Feb. 1, 2018

(65) Prior Publication Data

US 2018/0218877 A1    Aug. 2, 2018

(30) Foreign Application Priority Data

Feb. 2, 2017    (DE) .................. 10 2017 201 706

(51) Int. Cl.
*H01J 37/22*    (2006.01)
*G01N 15/14*    (2006.01)
(Continued)

(52) U.S. Cl.
CPC ........ *H01J 37/226* (2013.01); *G01N 15/1436* (2013.01); *G01N 23/225* (2013.01);
(Continued)

(58) Field of Classification Search
CPC ........ H01J 37/18; H01J 37/226; H01J 37/244; H01J 37/28; H01J 2237/182;
(Continued)

(56) References Cited

U.S. PATENT DOCUMENTS

2006/0076503 A1* 4/2006 Tsao ............... H01J 37/228
                                                250/396 R
2008/0315120 A1* 12/2008 Albiez ............. H01J 37/20
                                                250/491.1
(Continued)

OTHER PUBLICATIONS

Deben, "SEM TV Chamberscope system," Deben UK Ltd. (retrieved as PDF doc on Aug. 26, 2016).
Article "LED—Weisslicht" from www.bbernstaedt.de, retrieved on Aug. 26, 2016 (with English translation).

*Primary Examiner* — David E Smith
(74) *Attorney, Agent, or Firm* — Muirhead and Saturnelli, LLC

(57) ABSTRACT

The system described herein relates to an imaging device for imaging an object in a particle beam apparatus and/or for imaging a structural unit of a particle beam apparatus, and to a particle beam apparatus having such an imaging device. The imaging device has an illumination unit having a first switching state and a second switching state for illuminating the object and/or the structural unit with illumination light, where, in the first switching state, the illumination light comprises only light of a first spectral range and where, in the second switching state, the illumination light comprises only light of a second spectral range. The imaging device has a control unit for switching the illumination unit into the first switching state or into the second switching state, and a camera unit for imaging the object and/or the structural unit.

17 Claims, 8 Drawing Sheets

(51) Int. Cl.
*G01N 23/225* (2018.01)
*G01T 1/16* (2006.01)
*H01J 37/18* (2006.01)
*H01J 37/244* (2006.01)
*H01J 37/28* (2006.01)

(52) U.S. Cl.
CPC ............... *G01T 1/16* (2013.01); *H01J 37/18* (2013.01); *H01J 37/244* (2013.01); *H01J 37/28* (2013.01); *H01J 2237/182* (2013.01); *H01J 2237/2448* (2013.01); *H01J 2237/2608* (2013.01); *H01J 2237/2801* (2013.01); *H01J 2237/2806* (2013.01)

(58) Field of Classification Search
CPC ....... H01J 2237/2448; H01J 2237/2601; H01J 2237/2801; H01J 2237/2806; G01N 15/1436; G01N 23/225; G01T 1/16
See application file for complete search history.

(56) References Cited

U.S. PATENT DOCUMENTS

| | | | |
|---|---|---|---|
| 2010/0163729 A1 | 7/2010 | Isozaki | |
| 2011/0204228 A1* | 8/2011 | Tsuno | H01J 37/224 250/310 |
| 2012/0001070 A1* | 1/2012 | Takagi | G02B 21/0004 250/310 |
| 2012/0006987 A1* | 1/2012 | Rue | G01J 3/0208 250/332 |
| 2012/0257720 A1* | 10/2012 | Anan | H01J 37/228 378/64 |
| 2013/0335817 A1* | 12/2013 | Isobe | G01N 23/2251 359/363 |
| 2014/0034830 A1* | 2/2014 | Castagna | H01J 37/26 250/307 |
| 2014/0226003 A1* | 8/2014 | Phaneuf | H01J 37/222 348/80 |

* cited by examiner

IMAGING DEVICE FOR IMAGING AN OBJECT AND FOR IMAGING A STRUCTURAL UNIT IN A PARTICLE BEAM APPARATUS

TECHNICAL FIELD

The system described herein relates to an imaging device for imaging an object in a particle beam apparatus and/or for imaging a structural unit of a particle beam apparatus and more particularly to a particle beam apparatus having an electron beam apparatus and/or an ion beam apparatus and to a method for operating the particle beam apparatus.

BACKGROUND

Electron beam apparatuses, in particular a scanning electron microscope (also referred to as SEM below) and/or a transmission electron microscope (also referred to as TEM below), are used to examine objects (also referred to as samples) in order to obtain knowledge in respect of the properties and behaviors of the objects under certain conditions.

In an SEM, an electron beam (also referred to as primary electron beam below) is generated by means of a beam generator and focused on an object to be examined by way of a beam guiding system. An objective lens is used for focusing purposes. The primary electron beam is guided in a grid-shaped manner over a surface of the object to be examined by way of a deflection device. Here, the electrons of the primary electron beam interact with the object to be examined. In particular interaction particles and/or interaction radiation is/are generated as a result of the interaction. By way of example, the interaction particles are electrons. In particular, electrons are emitted by the object—the so-called secondary electrons—and electrons of the primary electron beam are scattered back—the so-called backscattered electrons. The interaction particles form the so-called secondary beam and are detected by at least one particle detector. The particle detector generates detection signals which are used to generate an image of the object.

An imaging of the object to be examined is thus obtained.

By way of example, the interaction radiation is x-ray radiation or cathodoluminescence. It is detected for example with a radiation detector and is used in particular for examining the material composition of the object.

In the case of a TEM, a primary electron beam is likewise generated by means of a beam generator and focused on an object to be examined by means of a beam guiding system. The primary electron beam passes through the object to be examined. When the primary electron beam passes through the object to be examined, the electrons of the primary electron beam interact with the material of the object to be examined. The electrons passing through the object to be examined are imaged onto a luminescent screen or onto a detector—for example in the form of a camera—by a system comprising an objective. By way of example, the aforementioned system additionally also comprises a projection lens. Here, imaging may also take place in the scanning mode of a TEM. As a rule, such a TEM is referred to as STEM. Additionally, provision can be made for detecting electrons scattered back at the object to be examined and/or secondary electrons emitted by the object to be examined by means of a further detector in order to image an object to be examined.

The integration of the function of an STEM and an SEM in a single particle beam apparatus is known. It is therefore possible to carry out examinations of objects with an SEM function and/or with an STEM function using this particle beam apparatus.

Furthermore, the prior art has disclosed the practice of analyzing and/or processing an object in a particle beam apparatus using, on the one hand, electrons and, on the other hand, ions. By way of example, an electron beam column having the function of an SEM is arranged at the particle beam apparatus. Additionally, an ion beam column is arranged at the particle beam apparatus. Ions used for processing an object are generated by means of an ion beam generator arranged in the ion beam column. By way of example, material of the object is ablated or material is applied onto the object during the processing. The ions are additionally or alternatively used for imaging. The electron beam column with the SEM function serves, in particular, for examining further the processed or unprocessed object, but also for processing the object.

The above-mentioned particle beam apparatuses of the prior art each have a sample chamber in which an object that is to be analyzed and/or processed is arranged on a sample stage. It is furthermore known to arrange a plurality of different objects simultaneously at the sample stage so as to analyze and/or process them one after the other using the respective particle beam apparatus that has the sample chamber. The sample stage is embodied to be movable so as for positioning the object or objects in the sample chamber. A relative position of the object or objects with respect to an objective lens is set, for example. A known sample stage is embodied to be movable in three directions which are arranged perpendicular to one another. Moreover, the sample stage can be rotated about two rotational axes which are arranged perpendicular to one another.

It is known to operate the sample chamber in different pressure ranges. For example, the sample chamber is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the sample chamber is vacuum-sealed during an examination of the object or objects with the particle beam apparatus. For this reason, free view of the object or objects is therefore not easily possible.

To ensure view of the object or objects and to be able to position the object or objects in a controlled fashion using the sample stage, it is known to use an imaging device for imaging the object or objects and for generating an image of the object or objects. It is furthermore known to use the imaging device for imaging a structural unit of the particle beam apparatus. The structural unit is arranged, for example, in the sample chamber of the particle beam apparatus. The structural unit is in particular embodied in the form of a gas injection system, a micromanipulator, a detector that is embodied to be movable and/or a charge compensation unit. The known imaging device has a camera that is mounted at the sample chamber or in the sample chamber and images the object, the objects and/or the structural unit. It is thus possible, for example, to observe and set in a controlled manner the position of the object, the objects and/or the structural unit by observing the images generated by the camera. Two imaging devices are known from the prior art, which will be explained below.

The first known imaging device permits observation of an object and/or a structural unit, arranged at the sample stage, during a simultaneous imaging or processing of the object with the primary particle beam of a particle beam apparatus. In other words, the first imaging device permits observation of the object and/or the structural unit using the camera, while the primary particle beam is focused onto the object and while interaction particles and/or interaction radiation is/are detected using a detector or a plurality of detectors. The first imaging device has an illumination unit that generates infrared light. It is known to use infrared light having a wavelength of 950 nm. The infrared light is used to illuminate the object and/or the structural unit. The object and/or the structural unit is/are imaged using the camera which is sensitive to infrared light. The images of the object generated due to the imaging by way of the camera are then used to observe the object. Furthermore, the images of the structural unit generated due to the imaging by way of the camera are then used to observe the structural unit. The first known imaging device permits imaging of the object or the structural unit using the camera and simultaneous examination of the object with the primary particle beam of the particle beam apparatus, since the detector or the plurality of detectors for detecting the interaction particles and/or interaction radiation are influenced by the infrared light only to a minor extent, with the result that sufficient function of the detector or the plurality of detectors continues to be ensured. However, the first known imaging device has the disadvantage that only black-and-white images are generated using the camera of the first known imaging device. Color differences on the objects, object regions or structural units cannot be identified on the image generated with the first known imaging device. Color information that the object or the structural unit has/contains cannot be identified in the black-and-white image either.

The second known imaging device does not generate black-and-white images, but color images of an object arranged in the sample chamber at the sample stage, or color images of a structural unit that is arranged in the sample chamber. The second known imaging device has an illumination unit that is arranged at the sample chamber and introduces white light into the sample chamber. This white light is used to illuminate the object and/or the structural unit. A camera images the object and generates color images of the object. The camera additionally or alternatively images the structural unit and generates color images of the structural unit. However, imaging of the object or of the structural unit using the second known imaging device (and thus the generation of a color image) and detection of interaction particles and/or interaction radiation are not simultaneously possible, or are simultaneously possible only if the detectors for detecting the interaction particles/interaction radiation are arranged, connected and/or embodied in the particle beam apparatus such that they are not disturbed, or disturbed only to a minor extent, by the white light from the illumination unit. Generally, the second known imaging device is used only to generate a recording of an overview image in color, which can no longer be updated during the detection of the interaction particles and/or interaction radiation.

Accordingly, it is desirable to be able to specify an imaging device and a particle beam apparatus having such an imaging device which permits the recording and generation of images of an object or of a structural unit in a sample chamber of a particle beam apparatus in every operating state of the particle beam apparatus.

SUMMARY OF THE INVENTION

Features of the system described herein are evident from the following description, the appended claims and/or the appended figures.

The imaging device according to the system described herein is provided for imaging an object in a particle beam apparatus and/or for imaging a structural unit of the particle beam apparatus. By way of example, the structural unit of the particle beam apparatus is embodied in the form of a gas injection system, a micromanipulator, a detector that is embodied to be movable and/or a charge compensation unit. The invention is not restricted to the aforementioned structural units. Rather, each structural unit of the particle beam apparatus is utilizable for the invention. Provision is in particular made for the structural unit to be arranged in an object chamber—that is to say a sample chamber—of the particle beam apparatus.

By way of example, the particle beam apparatus is embodied as an electron beam apparatus and/or as an ion beam apparatus. The particle beam apparatus serves for analyzing, in particular for imaging, and/or for processing an object. Provision is made in particular for the particle beam apparatus to have a beam generator for generating a particle beam with charged primary particles. By way of example, the primary particles are electrons or ions. Furthermore, the particle beam apparatus has for example an objective lens for focusing the particle beam onto the object. Interaction particles and/or interaction radiation is/are generated in the case of an interaction between the particle beam and the object. The interaction particles are, for example, secondary particles, in particular secondary electrons, and/or backscattered particles, for example backscattered electrons. By way of example, the interaction radiation is embodied in the form of x-ray radiation or cathodoluminescence. The interaction radiation is detected, for example, using a radiation detector.

The imaging device according to the system described herein has at least one illumination unit. The illumination unit has a first switching state and a second switching state for illuminating the object and/or the structural unit with illumination light. In the first switching state, the illumination light comprises only light of a first spectral range. By way of example, the illumination light comprises only a specific wavelength of the first spectral range. Alternatively, provision is made, for example, for the illumination light to be a superposition of a first light having a first wavelength and a second light having a second wavelength, with the first wavelength and the second wavelength being in the first spectral range. In the second switching state, the illumination light comprises only light of a second spectral range. By way of example, the illumination light comprises only a specific wavelength of the second spectral range. Alternatively, provision is made, for example, for the illumination light to be a superposition of a third light having a third wavelength and a fourth light having a fourth wavelength, with the third wavelength and the fourth wavelength being in the second spectral range.

In other words, the illumination unit emits either light of a first spectral range or light of a second spectral range. In an embodiment of the system described herein, provision is made, for example, for the first spectral range and the second spectral range to overlap to a minor extent, with an overlap range being less than 20 nm, for example. In that embodiment, provision is then made, for example, for the light of the first spectral range to have a proportion of less than 10% or less than 5% or less than 1% of the wavelengths from the overlap range. In that embodiment, provision is furthermore made, for example, for the light of the second spectral range to have a proportion of less than 10% or less than 5% or less than 1% of the wavelengths from the overlap range. In a further embodiment of the system described herein, provision is made, for example, for the first spectral range and the second spectral range to differ. The first spectral range and the second spectral range in this embodiment have no shared intersection of wavelengths.

The object and/or the structural unit is/are illuminated with the corresponding light. The imaging device according to the system described herein furthermore has at least one control unit for switching the illumination unit into the first switching state or into the second switching state.

Moreover, the imaging device according to the system described herein has a camera unit for imaging the object and/or the structural unit with light of the first spectral range in the first switching state of the illumination unit or with light of the second spectral range in the second switching state of the illumination unit.

The imaging device according to the system described herein ensures that imaging of an object that is arranged, for example, in the sample chamber of a particle beam apparatus or imaging of a structural unit that is arranged, for example, in the sample chamber of the particle beam apparatus is possible with a camera in every operating state of the particle beam apparatus. For example, if imaging or examining an object arranged in the sample chamber with the particle beam of the particle beam apparatus does not take place, or if, for example, a detector used in the particle beam apparatus for detecting interaction particles and/or interaction radiation is not sensitive for the light of the first spectral range, cannot detect the light of the first spectral range due to its arrangement in the particle beam apparatus, or is switched off, the control unit switches the illumination unit into the first switching state, with the result that light of the first spectral range is guided onto the object and/or the structural unit. The first spectral range comprises, for example, only white light or only the wavelength range of visible light. It is possible in this case to record color images using the camera unit, with the result that objects or structural units that are marked or configured in color can also be easily identified. A color recording of an image of the object or the structural unit is consequently also possible if the detector used in the particle beam apparatus for detecting interaction particles and/or interaction radiation is not sensitive for light of the first spectral range, for example an Everhart-Thornley detector or an ion detector having a detection surface that is coated with metal and blocks light of the first spectral range, in particular white light. A color recording of an image of the object or the structural unit is consequently also possible if the detector used in the particle beam apparatus for detecting interaction particles and/or interaction radiation is arranged locally in the particle beam apparatus such that it is not influenced by light of the first spectral range. In both previously mentioned embodiments it is possible to simultaneously record a color image of the object and image and examine the object with the particle beam of the particle beam apparatus. It is furthermore possible to simultaneously record a color image of the structural unit and image and examine the object with the particle beam of the particle beam apparatus. A color recording of an image of the object or the structural unit is consequently also possible if the detector used in the particle beam apparatus for detecting interaction particles and/or interaction radiation is switched off.

However, if the detector for detecting the interaction particles or interaction radiation is disturbed by the light of the first spectral range in the first switching state of the illumination unit, the control unit switches the illumination unit into the second switching state. In the second switching state, light of the second spectral range is used for illuminating and imaging the object and/or the structural unit. The light of the second spectral range is infrared light, for example. The light of the second spectral range is configured such, for example, that it is possible to simultaneously record an image of the object and/or the structural unit using the camera unit of the imaging device according to the system described herein and detect the interaction particles or interaction radiation for examining and imaging the object with the particle beam of the particle beam apparatus.

The imaging device according to the system described herein ensures in particular that the object and/or the structural unit is/are observable in every operating state of the particle beam apparatus and the position of the object that is arranged, for example, at a sample stage of the particle beam apparatus and/or the position of the structural unit can be set in a controlled manner.

As already mentioned above, an embodiment of the imaging device according to the system described herein additionally or alternatively provides for the first spectral range to comprise only the wavelength range of visible light. By way of example, this is the wavelength range from 380 nm to 780 nm, including the range boundaries. In a further embodiment of the imaging device according to the system described herein, provision is additionally or alternatively made for the first spectral range to comprise only white light. In this configuration of the first spectral range it is ensured that good color recordings of the object and/or of the structural unit can be taken with the camera unit.

In a still further embodiment of the imaging device according to the system described herein, provision is additionally or alternatively made for the second spectral range to comprise only the wavelength range of infrared light. Provision is in particular made, for example, for the second spectral range to comprise only the wavelength range of near infrared light. By way of example, the second spectral range comprises only light of a wavelength range of 780 nm to 3 µm. This configuration of the second spectral range ensures that images of the object and/or of the structural unit can be recorded with the imaging device according to the system described herein, even if the object is simultaneously examined and/or processed with the particle beam of the particle beam apparatus. Owing to the use of the light of the second spectral range, this configuration also makes possible the recording of images of the object and/or the structural unit with the imaging device according to the system described herein if the detector for detecting the interaction particles and/or interaction radiation is configured, switched and/or arranged such that it would be disturbed by the light of the first spectral range were the light of the first spectral range used. The image generated with the imaging device according to the system described herein is in that case a black-and-white image.

In an embodiment of the imaging device according to the system described herein, provision is additionally or alternatively made for the control unit to set and/or control the intensity of the light of the first spectral range and/or of the light of the second spectral range. In other words, the control unit is embodied for setting and/or controlling the intensity of the light of the first spectral range and/or the light of the second spectral range. This embodiment ensures that disturbing influences on a particle detector in the particle beam apparatus can be minimized and at the same time good imaging of the object and/or of the structural unit with the imaging device is ensured.

In one embodiment of the imaging device according to the system described herein, provision is additionally or alternatively made for the imaging device to have at least one first light-emitting unit for generating the light of the first spectral range. Provision is in particular made for the first light-emitting unit to additionally have a first filter unit. The first filter unit is configured, for example, such that light having a wavelength that does not fall into the first spectral range is filtered out of the light generated by the first light-emitting unit. Provision is alternatively made for the first light-emitting unit to generate only light of the first spectral range. In a further embodiment of the imaging device according to the system described herein, provision is made for the first light-emitting unit to have at least one LED and/or to be embodied in the form of an LED. The LED is in particular embodied in the form of an LED that emits white light. By way of example, this is an LED operating on the principle of luminescence wavelength conversion. Emitted blue radiation components of the LED are used to be partially converted into yellow light using a phosphor admixture. The generated spectra in sum give white light. Provision is additionally or alternatively made for the first light-emitting unit to have a plurality of LEDs, for example at least one first LED and/or at least one second LED and/or at least one third LED. Provision is made in particular for the first LED to be embodied in the form of an LED that emits red light, for the second LED to be embodied in the form of an LED that emits green light, and for the third LED to be embodied in the form of an LED that emits blue light. By mixing the red, green and blue light, light is generated that is perceived as white light.

In a further embodiment of the imaging device according to the system described herein, provision is additionally or alternatively made for the imaging device to have at least one second light-emitting unit for generating the light of the second spectral range. Provision is in particular made for the second light-emitting unit to additionally have a second filter unit. The second filter unit is configured, for example, such that light having a wavelength that does not fall into the second spectral range is filtered out of the light generated by the second light-emitting unit. Provision is alternatively made for the second light-emitting unit to generate only light of the second spectral range. In a further embodiment of the imaging device according to the system described herein, provision is made for the second light-emitting unit to have at least one LED and/or to be embodied in the form of an LED. This LED is embodied for example in the form of an infrared LED that emits light in the near infrared range. Provision is in particular made for the infrared LED to emit infrared light having a wavelength of 800 nm to 1000 nm. By way of example, an infrared LED is used that has a wavelength of 950 nm. It is explicitly noted that the invention is not limited to these wavelengths. Rather, any wavelength that is suitable for performing the invention can be used for the light of the second spectral range.

In yet another embodiment of the imaging device according to the system described herein, provision is additionally or alternatively made for the camera unit to have at least one detection unit with a detector sensitivity. The detector sensitivity is configured both for the light of the first spectral range in the first switching state of the illumination unit and also for the light of the second spectral range in the second switching state of the illumination unit. In other words, the detection unit of the camera unit detects both light of the first spectral range and light of the second spectral range.

In yet another embodiment of the imaging device according to the system described herein, provision is additionally or alternatively made for the camera unit to have at least one CCD or at least one CMOS.

The system described herein also relates to a particle beam apparatus. By way of example, the particle beam apparatus according to the system described herein is embodied as an electron beam apparatus and/or as an ion beam apparatus. The particle beam apparatus according to the system described herein serves for analyzing, in particular for imaging, and/or for processing an object. The particle beam apparatus according to the system described herein has at least one beam generator for generating a particle beam comprising charged primary particles. By way of example, the primary particles are electrons or ions. The particle beam apparatus according to the system described herein furthermore has at least one objective lens for focusing the particle beam onto the object, wherein interaction particles and/or interaction radiation is/are generated upon interaction between the particle beam and the object. The interaction particles are, for example, secondary particles, in particular secondary electrons, and/or backscattered particles, for example backscattered electrons. By way of example, the interaction radiation is x-ray radiation or cathodoluminescence. Furthermore, the particle beam apparatus according to the system described herein has at least one detector for detecting the interaction particles and/or interaction radiation. Furthermore, the particle beam apparatus according to the system described herein is provided with an imaging device for imaging the object and/or for imaging a structural unit of the particle beam apparatus, wherein the imaging device has at least one of the features mentioned above or further below or a combination of at least two of the features mentioned above or further below. The particle beam apparatus according to the system described herein has the same advantages as the imaging device according to the system described herein.

In an embodiment of the particle beam apparatus according to the system described herein, provision is additionally or alternatively made for the particle beam apparatus to have at least one mirror corrector for correcting chromatic and/or spherical aberration.

As already mentioned above, provision is additionally or alternatively made in a further embodiment of the particle beam apparatus according to the system described herein for the particle beam apparatus to be embodied as an electron beam apparatus and/or as an ion beam apparatus.

In yet a further embodiment of the particle beam apparatus according to the system described herein, it is additionally or alternatively provided that the beam generator for generating a particle beam comprising charged primary particles is designed as a first beam generator for generating a first particle beam comprising first charged primary particles and the objective lens is designed as a first objective lens for focusing the first particle beam onto the object. Furthermore, the particle beam apparatus has at least one second beam generator for generating a second particle beam comprising second charged primary particles, and at least one second objective lens for focusing the second particle beam onto the object. The second charged primary particles are electrons or ions, for example.

In an embodiment of the particle beam apparatus according to the system described herein, provision is additionally or alternatively made for the structural unit to be embodied in particular as a gas injection system, a micromanipulator, a detector that is embodied to be movable, and/or a charge compensation unit. The invention is not restricted to the aforementioned structural units. Rather, each structural unit of the particle beam apparatus is utilizable for the system described herein. Provision is in particular made for the structural unit to be arranged in an object chamber—that is to say a sample chamber—of the particle beam apparatus.

The system described herein also relates to a method for operating the particle beam apparatus, having at least one of the features specified further above or yet to be specified below or with a combination of at least two of the features specified further above or yet to be specified below. In the method according to the system described herein, provision is made for the control unit to switch the illumination unit into the first switching state or into the second switching state. In the first switching state, the object and/or the structural unit is/are imaged by way of the camera unit with the light of the first spectral range. In the second switching state, the object and/or the structural unit is/are imaged by way of the camera unit with the light of the second spectral range. In an embodiment of the method according to the system described herein, provision is additionally or alternatively made for the particle beam to be guided away from the object or be switched off in the first switching state. This is provided in particular if a color image of the object is intended to be made, as already mentioned above.

In a further embodiment of the method according to the system described herein, provision is additionally or alternatively made for the intensity of the light of the first spectral range and/or the intensity of the light of the second spectral range to be set.

In yet another embodiment of the method according to the system described herein, provision is additionally or alternatively made for the detector to be switched off in the first switching state. Provision is additionally or alternatively made for the detector to be moved into a position such that no light of the first spectral range is incident on the detector in the first switching state. Provision is again additionally or alternatively made for the detector to be moved into a position such that only a minimum intensity of the light of the first spectral range is incident on the detector in the first switching state. Provision is additionally or alternatively made for the detector to be switched off. In all previously mentioned cases, it is then possible to furthermore generate color images of the object and/or of the structural unit with light of the first spectral range.

BRIEF DESCRIPTION OF DRAWINGS

The system described herein will be explained in more detail below on the basis of exemplary embodiments using drawings. In the figures.

DETAILED DESCRIPTION OF VARIOUS EMBODIMENTS

The system described herein is now explained in more detail by means of particle beam apparatuses in the form of an SEM and in the form of a combination apparatus, which has an electron beam column and an ion beam column. Reference is explicitly made to the fact that the system described herein may be used in any particle beam apparatus, in particular in every electron beam apparatus and/or in every ion beam apparatus.

Figure 1:
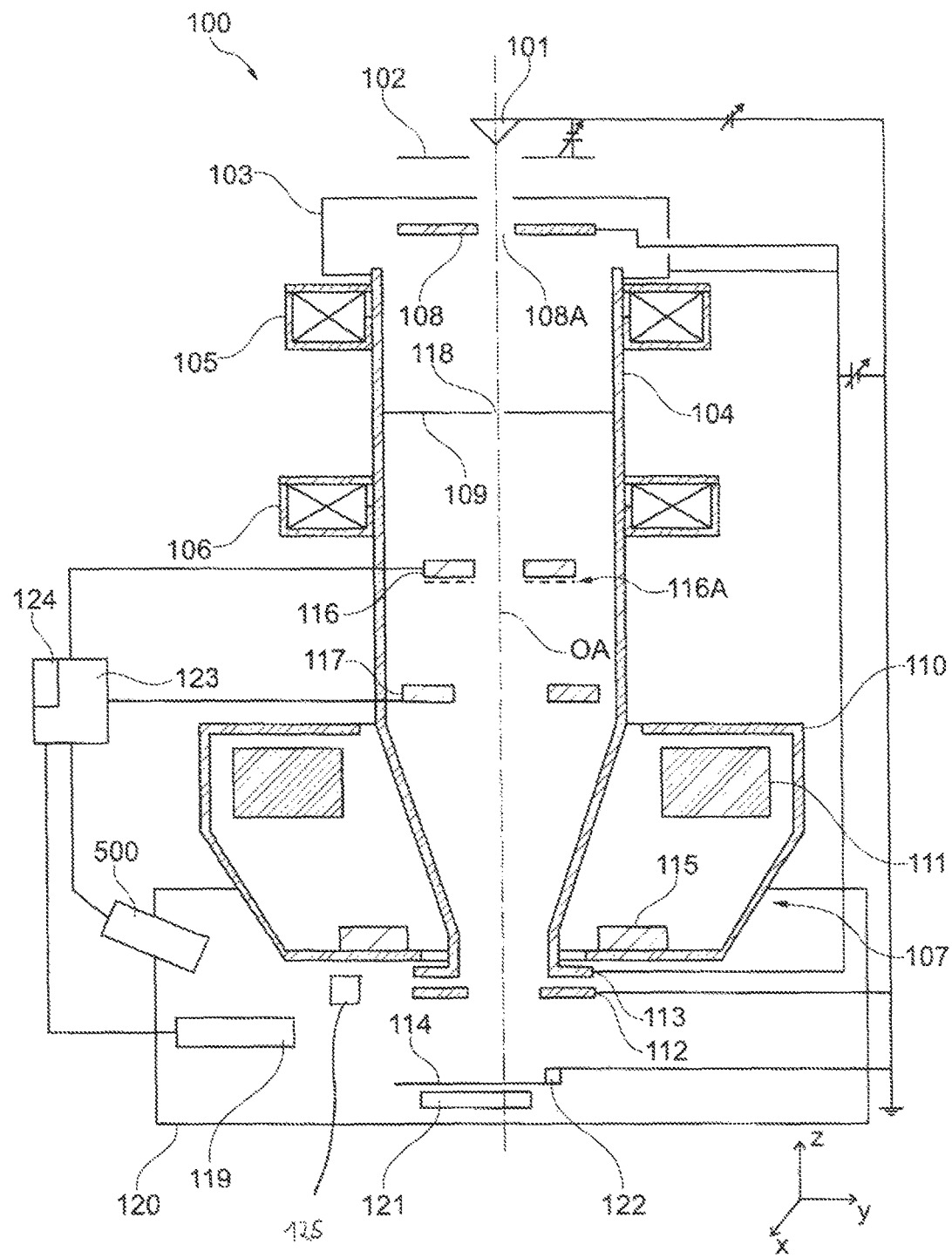
FIG. 1 shows a first exemplary embodiment of a particle beam apparatus according to the system described herein.

FIG. 1 shows a schematic illustration of an SEM 100. The SEM 100 comprises a first beam generator in the form of an electron source 101, which is embodied as a cathode. Further, the SEM 100 is provided with an extraction electrode 102 and with an anode 103, which is placed onto one end of a beam guiding tube 104 of the SEM 100. By way of example, the electron source 101 is embodied as a thermal field emitter. However, the invention is not restricted to such an electron source 101. Rather, any electron source is utilizable.

Electrons emerging from the electron source 101 form a primary electron beam. The electrons are accelerated to the anode potential due to a potential difference between the electron source 101 and the anode 103. In the exemplary embodiment depicted here, the anode potential is 1 kV to 20 kV, e.g. 5 kV to 15 kV, in particular 8 kV, in relation to a ground potential of a housing of a sample chamber 120. However, alternatively it could be at ground potential.

Two condenser lenses, namely a first condenser lens 105 and a second condenser lens 106, are arranged at the beam guiding tube 104. Here, proceeding from the electron source 101 as viewed in the direction of a first objective lens 107, the first condenser lens 105 is arranged first, followed by the second condenser lens 106. Reference is explicitly made to the fact that further exemplary embodiments of the SEM 100 may have only a single condenser lens. A first aperture unit 108 is arranged between the anode 103 and the first condenser lens 105. Together with the anode 103 and the beam guiding tube 104, the first aperture unit 108 is at a high voltage potential, namely the potential of the anode 103, or it is connected to ground. The first aperture unit 108 has numerous first apertures 108A, of which one is depicted in FIG. 1. Two first apertures 108A are present, for example. Each one of the numerous first apertures 108A has a different aperture diameter. By means of an adjustment mechanism (not depicted here), it is possible to set a desired first aperture 108A onto an optical axis OA of the SEM 100. Reference is explicitly made to the fact that, in further exemplary embodiments, the first aperture unit 108 may be provided with only a single aperture 108A. In this exemplary embodiment, an adjustment mechanism may be omitted. The first aperture unit 108 is then designed in a stationary fashion. A stationary second aperture unit 109 is arranged between the first condenser lens 105 and the second condenser lens 106. The second aperture unit 109 may be designed in a movable fashion as an alternative thereto.

The first objective lens 107 has pole pieces 110, in which a bore is formed. The beam guiding tube 104 is guided through this bore. Further, coils 111 are arranged in the pole pieces 110.

An electrostatic retardation device is arranged in a lower region of the beam guiding tube 104. It has a single electrode 112 and a tube electrode 113. The tube electrode 113 is arranged at one end of the beam guiding tube 104, which faces an object 114. Together with the beam guiding tube 104, the tube electrode 113 is at the potential of the anode 103, while the single electrode 112 and the object 114 are at a lower potential in relation to the potential of the anode 103. In the present case, this is the ground potential of the housing of the sample chamber 120. In this manner, the electrons of the primary electron beam may be decelerated to a desired energy which is required for examining the object 114.

The SEM 100 further comprises a scanning device 115, by means of which the primary electron beam may be deflected and scanned over the object 114. Here, the electrons of the primary electron beam interact with the object 114. As a result of the interaction, interaction particles are generated, which are detected. In particular, electrons are emitted from the surface of the object 114—the so-called secondary electrons—or electrons of the primary electron beam are scattered back—the so-called backscattered electrons—as interaction particles.

The object 114 and the individual electrode 112 may also be at different potentials and potentials different than ground. It is thereby possible to set the location of the retardation of the primary electron beam in relation to the object 114. By way of example, if the retardation is carried out very near to the object 114, optical aberrations become smaller.

A detector arrangement comprising a first detector 116 and a second detector 117 is arranged in the beam guiding tube 104 for detecting the secondary electrons and/or the backscattered electrons. Here, the first detector 116 is arranged on the source-side along the optical axis OA, while the second detector 117 is arranged on the object-side along the optical axis OA in the beam guiding tube 104. The first detector 116 and the second detector 117 are arranged offset from one another in the direction of the optical axis OA of the SEM 100. Both the first detector 116 and the second detector 117 each have a passage opening, through which the primary electron beam may pass. The first detector 116 and the second detector 117 are approximately at the potential of the anode 103 and of the beam guiding tube 104. The optical axis OA of the SEM 100 extends through the respective passage openings.

The second detector 117 serves principally for detecting secondary electrons. Upon emerging from the object 114, the secondary electrons initially have a low kinetic energy and arbitrary directions of motion. By means of the strong extraction field emanating from the tube electrode 113, the secondary electrons are accelerated in the direction of the first objective lens 107. The secondary electrons enter the first objective lens 107 approximately parallel. The beam diameter of the beam of secondary electrons remains small in the first objective lens 107 as well. The first objective lens 107 then has a strong effect on the secondary electrons and generates a comparatively short focus of the secondary electrons with sufficiently steep angles with respect to the optical axis OA, such that the secondary electrons diverge far apart from one another downstream of the focus and are incident on the second detector 117 on the active area thereof. By contrast, only a small proportion of electrons that are backscattered at the object 114—that is to say backscattered electrons which have a relatively high kinetic energy in comparison with the secondary electrons upon emerging from the object 114—are detected by the second detector 117. The high kinetic energy and the angles of the backscattered electrons with respect to the optical axis OA upon emerging from the object 114 have the effect that a beam waist, that is to say a beam region having a minimum diameter, of the backscattered electrons lies in the vicinity of the second detector 117. A large portion of the backscattered electrons passes through the passage opening of the second detector 117. Therefore, the first detector 116 substantially serves to detect the backscattered electrons.

In a further embodiment of the SEM 100, the first detector 116 may additionally be embodied with an opposing field grating 116A. The opposing field grating 116A is arranged at the side of the first detector 116 directed toward the object 114. With respect to the potential of the beam guiding tube 104, the opposing field grating 116A has a negative potential such that only backscattered electrons with a high energy pass through the opposing field grating 116A to the first detector 116. Additionally or alternatively, the second detector 117 has a further opposing field grating, which has an analogous embodiment to the aforementioned opposing field grating 116A of the first detector 116 and which has an analogous function.

The SEM 100 furthermore has in the sample chamber 120 a chamber detector 119, for example an Everhart-Thornley detector or an ion detector which has a detection surface that is coated with metal and blocks light, in particular white light.

The detection signals generated by the first detector 116 and the second detector 117 are used to generate an image or images of the surface of the object 114.

Reference is explicitly made to the fact that the apertures of the first aperture unit 108 and of the second aperture unit 109, as well as the passage openings of the first detector 116 and of the second detector 117 are depicted in exaggerated fashion. The passage opening of the first detector 116 and of the second detector 117 have an extent perpendicular to the optical axis OA in the range of 0.5 mm to 5 mm. By way of example, they are of circular design and have a diameter in the range of 1 mm to 3 mm perpendicular to the optical axis OA.

The second aperture unit 109 is configured as a pinhole aperture in the exemplary embodiment depicted here and is provided with a second aperture 118 for the passage of the primary electron beam, which has an extent in the range from 5 µm to 500 µm, e.g. 35 µm. As an alternative thereto, provision is made in a further embodiment for the second aperture unit 109 to be provided with a plurality of apertures, which can be displaced mechanically with respect to the primary electron beam or which can be reached by the primary electron beam by the use of electrical and/or magnetic deflection elements. The second aperture unit 109 is embodied as a pressure stage unit. It separates a first region, in which the electron source 101 is arranged and in which an ultra-high vacuum ($10^{-7}$ hPa to $10^{-12}$ hPa) prevails, from a second region, which has a high vacuum ($10^{-3}$ hPa to $10^{-7}$ hPa). The second region is the intermediate pressure region of the beam guiding tube 104, which leads to the sample chamber 120.

The sample chamber 120 is under vacuum. To generate the vacuum, a pump (not illustrated) is arranged at the sample chamber 120. In the exemplary embodiment illustrated in FIG. 1, the sample chamber 120 is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the sample chamber 120 is vacuum-sealed.

The object 114 is arranged at a sample stage 122. The sample stage 122 is embodied to be movable in three directions arranged perpendicular to one another, namely in an x-direction, in a y-direction and in a z-direction. Moreover, the sample stage 122 can be rotated about two rotational axes which are arranged perpendicular to one another.

The SEM 100 further comprises a third detector 121, which is arranged in the sample chamber 120. More precisely, the third detector 121 is arranged behind the object 114, as seen from the electron source 101 along the optical axis OA. The primary electron beam passes through the object 114 to be examined. When the primary electron beam passes through the object 114 to be examined, the electrons of the primary electron beam interact with the material of the object 114 to be examined. The electrons passing through the object 114 to be examined are detected by the third detector 121.

A structural unit 125 of the SEM 100 is arranged in the sample chamber 120. By way of example, the structural unit 125 is embodied in the form of a gas injection system, a micromanipulator, a further detector that is embodied to be movable and/or a charge compensation unit. The invention is not restricted to the aforementioned structural units. Rather, each structural unit of the SEM 100 is utilizable for the invention.

Arranged at the sample chamber 120 is an imaging device 500, which will be discussed in more detail further below. The imaging device 500, the first detector 116, the second detector 117 and the chamber detector 119 are connected to a monitoring unit 123, which has a monitor 124. The third detector 121 is also connected to the monitoring unit 123. For reasons of clarity, this is not illustrated. The monitoring unit 123 processes detection signals generated by the first detector 116, the second detector 117, the chamber detector 119 and/or the third detector 121 and represents them on the monitor 124 in the form of images. Moreover, the monitor 124 serves for displaying images generated with the imaging device 500. This is discussed in more detail further below.

Figure 2:
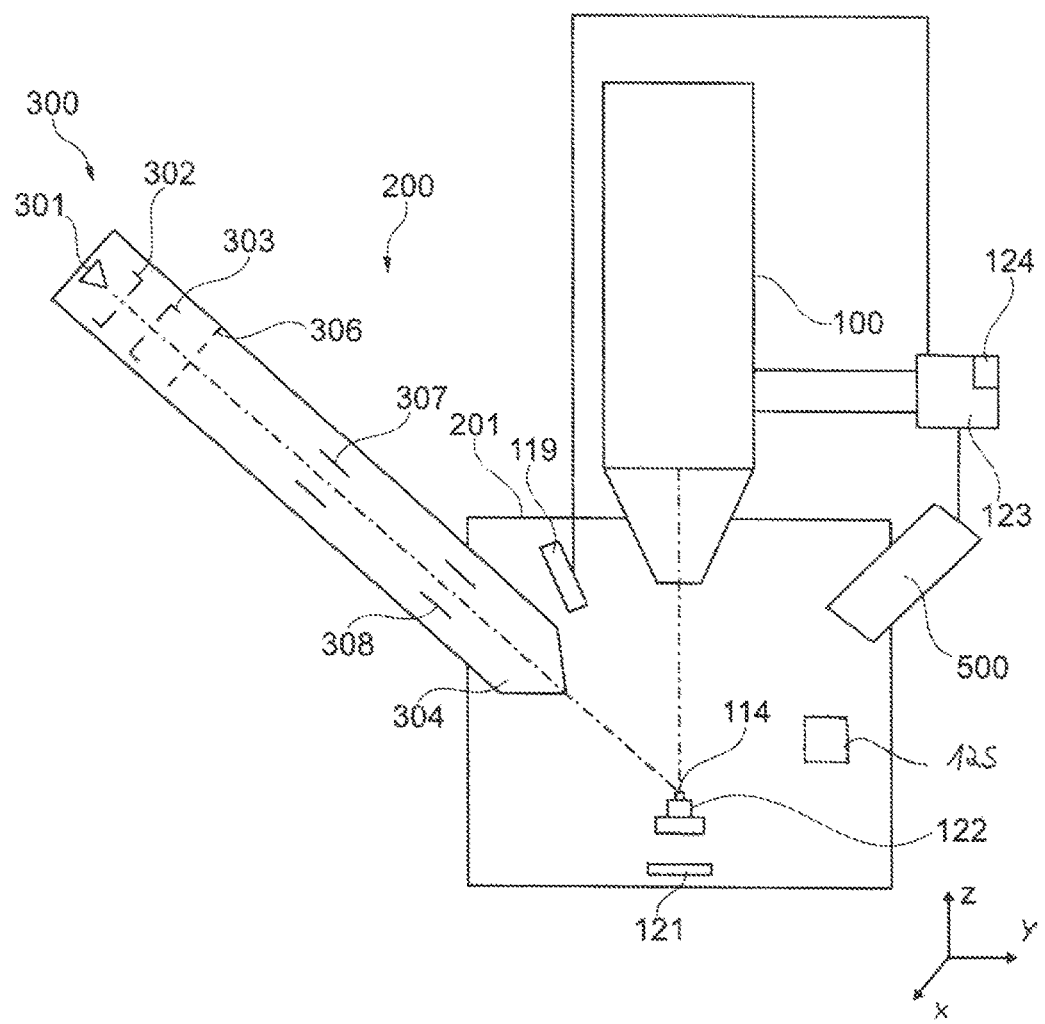
FIG. 2 shows a second exemplary embodiment of a particle beam apparatus according to the system described herein.

FIG. 2 shows a particle beam apparatus in the form of a combination apparatus 200. The combination apparatus 200 has two particle beam columns. On the one hand, the combination apparatus 200 is provided with the SEM 100, as already depicted in FIG. 1, but without the sample chamber 120. Rather, the SEM 100 is arranged at a sample chamber 201. The sample chamber 201 is under vacuum. To generate the vacuum, a pump (not illustrated) is arranged at the sample chamber 201. In the exemplary embodiment illustrated in FIG. 2, the sample chamber 201 is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the sample chamber 201 is vacuum-sealed.

Arranged in the sample chamber 201 is a chamber detector 119 which is embodied, for example, in the form of an Everhart-Thornley detector or an ion detector and which has a detection surface coated with metal that blocks light, in particular white light.

The SEM 100 serves to generate a first particle beam, namely the primary electron beam already described further above. On the other hand, the combination apparatus 200 is provided with an ion beam apparatus 300, which is likewise arranged at the sample chamber 201.

The SEM 100 is arranged vertically in relation to the sample chamber 201. By contrast, the ion beam apparatus 300 is arranged inclined by an angle of approximately 50° in relation to the SEM 100. It has a second beam generator in the form of an ion beam generator 301. Ions, which form a second particle beam in the form of an ion beam, are generated by the ion beam generator 301. The ions are accelerated by means of an extraction electrode 302, which is at a predeterminable potential. The second particle beam then passes through ion optics of the ion beam apparatus 300, wherein the ion optics comprise a condenser lens 303 and a second objective lens 304. The second objective lens 304 ultimately generates an ion probe, which is focused on the object 114 arranged at a sample stage 122.

An adjustable or selectable aperture 306, a first electrode arrangement 307 and a second electrode arrangement 308 are arranged above the second objective lens 304 (i.e. in the direction of the ion beam generator 301), wherein the first electrode arrangement 307 and the second electrode arrangement 308 are embodied as scanning electrodes. The second particle beam is scanned over the surface of the object 114 by means of the first electrode arrangement 307 and the second electrode arrangement 308, with the first electrode arrangement 307 acting in a first direction and the second electrode arrangement 308 acting in a second direction, which is counter to the first direction. Using this, scanning is carried out in e.g. an x-direction. The scanning in a y-direction perpendicular thereto is brought about by further electrodes (not depicted here), which are rotated by 90°, at the first electrode arrangement 307 and at the second electrode arrangement 308.

As discussed above, the object 114 is arranged at the sample stage 122. In the exemplary embodiment shown in FIG. 2, the sample stage 122 is also embodied to be movable in three directions arranged perpendicular to one another, namely in an x-direction, in a y-direction and in a z-direction. Moreover, the sample stage 122 can be rotated about two rotational axes which are arranged perpendicular to one another.

The distances depicted in FIG. 2 between the individual units of the combination apparatus 200 are depicted in exaggerated fashion in order to better depict the individual units of the combination apparatus 200.

A structural unit 125 of the combination apparatus 200 is arranged in the sample chamber 201. By way of example, the structural unit 125 is embodied in the form of a gas injection system, a micromanipulator, a further detector that is embodied to be movable and/or a charge compensation unit. The invention is not restricted to the aforementioned structural units. Rather, each structural unit of the combination apparatus 200 is utilizable for the invention.

Arranged at the sample chamber 201 is an imaging device 500, which will be discussed in more detail further below. The imaging device 500 is connected to a monitoring unit 123, which has a monitor 124. The monitoring unit 123 processes detection signals generated by the first detector 116, the second detector 117 (not depicted in FIG. 2), the chamber detector 119 and/or the third detector 121 and represents them on the monitor 124 in the form of images. Moreover, the monitor 124 serves for displaying images generated with the imaging device 500. This is discussed in more detail further below.

Figure 3:
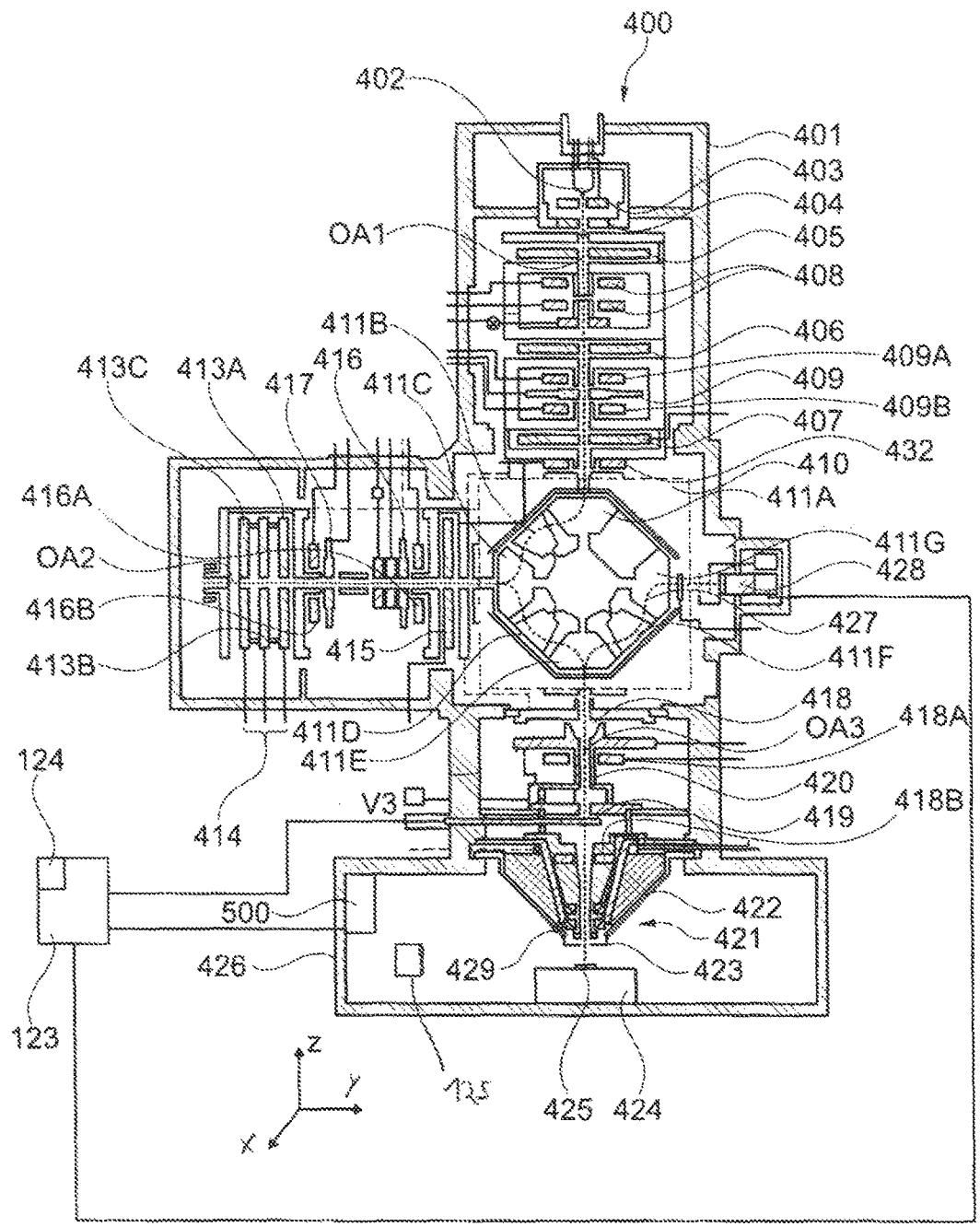
FIG. 3 shows a third exemplary embodiment of a particle beam apparatus according to the system described herein.

FIG. 3 is a schematic illustration of a further exemplary embodiment of a particle beam apparatus according to the system described herein. This exemplary embodiment of the particle beam apparatus is provided with the reference sign 400 and comprises a mirror corrector for correcting e.g. chromatic and/or spherical aberrations. The particle beam apparatus 400 comprises a particle beam column 401, which is embodied as an electron beam column and substantially corresponds to an electron beam column of a corrected SEM. However, the particle beam apparatus 400 is not restricted to an SEM with a mirror corrector. Rather, the particle beam apparatus may comprise any type of correction units.

The particle beam column 401 comprises a particle beam generator in the form of an electron source 402 (cathode), an extraction electrode 403, and an anode 404. By way of example, the electron source 402 is embodied as a thermal field emitter. Electrons emerging from the electron source 402 are accelerated to the anode 404 due to a potential difference between the electron source 402 and the anode 404. Accordingly, a particle beam in the form of an electron beam is formed along a first optical axis OA1.

The particle beam is guided along a beam path, which corresponds to the first optical axis OA1, after the particle beam has emerged from the electron source 402. A first electrostatic lens 405, a second electrostatic lens 406, and a third electrostatic lens 407 are used to guide the particle beam.

Furthermore, the particle beam is adjusted along the beam path using a beam guiding device. The beam guiding device of this exemplary embodiment comprises a source adjustment unit with two magnetic deflection units 408 arranged along the first optical axis OA1. Moreover, the particle beam apparatus 400 comprises electrostatic beam deflection units. A first electrostatic beam deflection unit 409, which is also embodied as a quadrupole in a further embodiment, is arranged between the second electrostatic lens 406 and the third electrostatic lens 407. The first electrostatic beam deflection unit 409 is likewise arranged downstream of the magnetic deflection units 408. A first multi-pole unit 409A in the form of a first magnetic deflection unit is arranged at one side of the first electrostatic beam deflection unit 409. Moreover, a second multi-pole unit 409B in the form of a second magnetic deflection unit is arranged at the other side of the first electrostatic beam deflection unit 409. The first electrostatic beam deflection unit 409, the first multi-pole unit 409A, and the second multi-pole unit 409B are set for the purposes of setting the particle beam in respect of the axis of the third electrostatic lens 407 and the entrance window of a beam deflection device 410. The first electrostatic beam deflection unit 409, the first multi-pole unit 409A and the second multi-pole unit 409B may interact like a Wien filter. A further magnetic deflection element 432 is arranged at the entrance to the beam deflection device 410.

The beam deflection device 410 is used as a particle beam deflector, which deflects the particle beam in a specific manner. The beam deflection device 410 comprises a plurality of magnetic sectors, namely a first magnetic sector 411A, a second magnetic sector 411B, a third magnetic sector 411C, a fourth magnetic sector 411D, a fifth magnetic sector 411E, a sixth magnetic sector 411F, and a seventh magnetic sector 411G. The particle beam enters the beam deflection device 410 along the first optical axis OA1 and is deflected by the beam deflection device 410 in the direction of a second optical axis OA2. The beam deflection is performed by means of the first magnetic sector 411A, by means of the second magnetic sector 411B and by means of the third magnetic sector 411C through an angle of 30° to 120°. The second optical axis OA2 is oriented at the same angle with respect to the first optical axis OA1. The beam deflection device 410 also deflects the particle beam which is guided along the second optical axis OA2, to be precise in the direction of a third optical axis OA3. The beam deflection is provided by the third magnetic sector 411C, the fourth magnetic sector 411D, and the fifth magnetic sector 411E. In the exemplary embodiment in FIG. 3, the deflection with respect to the second optical axis OA2 and with respect to the third optical axis OA3 is provided by deflecting the particle beam at an angle of 90°. Hence, the third optical axis OA3 extends coaxially with respect to the first optical axis OA1. However, reference is made to the fact that the particle beam apparatus 400 according to the invention described here is not restricted to deflection angles of 90°. Rather, any suitable deflection angle may be selected by the beam deflection device 410, for example 70° or 110°, such that the first optical axis OA1 does not extend coaxially with respect to the third optical axis OA3. In respect of further details of the beam deflection device 410, reference is made to WO 2002/067286 A2.

After the particle beam was deflected by the first magnetic sector 411A, the second magnetic sector 411B, and the third magnetic sector 411C, the particle beam is guided along the second optical axis OA2. The particle beam is guided to an electrostatic mirror 414 and travels on its path to the electrostatic mirror 414 along a fourth electrostatic lens 415, a third multi-pole unit 416A in the form of a magnetic deflection unit, a second electrostatic beam deflection unit 416, a third electrostatic beam deflection unit 417, and a fourth multi-pole unit 416B in the form of a magnetic deflection unit. The electrostatic mirror 414 comprises a first mirror electrode 413A, a second mirror electrode 413B, and a third mirror electrode 413C. Electrons of the particle beam which are reflected back at the electrostatic mirror 414 once again travel along the second optical axis OA2 and re-enter the beam deflection device 410. Then, they are deflected to the third optical axis OA3 by the third magnetic sector 411C, the fourth magnetic sector 411D, and the fifth magnetic sector 411E.

The electrons of the particle beam emerge from the beam deflection device 410 and are guided along the third optical axis OA3 to the object 425 which is intended to be examined. On the path to the object 425, the particle beam is guided to a fifth electrostatic lens 418, a beam guiding tube 420, a fifth multi-pole unit 418A, a sixth multi-pole unit 418B, and an objective lens 421. The fifth electrostatic lens 418 is an electrostatic immersion lens. By way of the fifth electrostatic lens 418, the particle beam is decelerated or accelerated to an electric potential of the beam guiding tube 420.

By means of the objective lens 421, the particle beam is focused in a focal plane in which the object 425 is arranged. The object 425 is arranged at a movable sample stage 424. The movable sample stage 424 is arranged in a sample chamber 426 of the particle beam apparatus 400. The sample stage 424 is embodied to be movable in three directions arranged perpendicular to one another, namely in an x-direction, in a y-direction and in a z-direction. Moreover, the sample stage 424 can be rotated about two rotational axes which are arranged perpendicular to one another. The sample chamber 426 is under vacuum. To generate the vacuum, a pump (not illustrated) is arranged at the sample chamber 426. In the exemplary embodiment illustrated in FIG. 3, the sample chamber 426 is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the sample chamber 426 is vacuum-sealed.

The objective lens 421 may be embodied as a combination of a magnetic lens 422 and a sixth electrostatic lens 423. The end of the beam guiding tube 420 further may be an electrode of an electrostatic lens. After emerging from the beam guiding tube 420, particles of the particle beam apparatus are decelerated to a potential of the object 425 arranged on the sample stage 424. The objective lens 421 is not restricted to a combination of the magnetic lens 422 and the sixth electrostatic lens 423. Rather, the objective lens 421 may assume any suitable form. By way of example, the objective lens 421 also may be embodied as a purely magnetic lens or as a purely electrostatic lens.

The particle beam which is focused onto the object 425 interacts with the object 425. Interaction particles are generated. In particular, secondary electrons are emitted from the object 425 or backscattered electrons are scattered back at the object 425. The secondary electrons or the backscattered electrons are accelerated again and guided into the beam guiding tube 420 along the third optical axis OA3. In particular, the trajectories of the secondary electrons and the backscattered electrons extend on the route of the beam path of the particle beam in the opposite direction to the particle beam.

The particle beam apparatus 400 comprises a first analysis detector 419 which is arranged between the beam deflection device 410 and the objective lens 421 along the beam path. Secondary electrons traveling in directions oriented at a large angle with respect to the third optical axis OA3 are detected by the first analysis detector 419. Backscattered electrons and secondary electrons which have a small axial distance with respect to the third optical axis OA3 at the location of the first analysis detector 419—i.e. backscattered electrons and secondary electrons which have a small distance from the third optical axis OA3 at the location of the first analysis detector 419—enter the beam deflection device 410 and are deflected to a second analysis detector 428 by the fifth magnetic sector 411E, the sixth magnetic sector 411F and the seventh magnetic sector 411G along a detection beam path 427. By way of example, the deflection angle is 90° or 110°.

The first analysis detector 419 generates detection signals which are largely generated by emitted secondary electrons. The detection signals which are generated by the first analysis detector 419 are supplied to a monitoring unit 123 and used to obtain information about the properties of the interaction region of the focused particle beam with the object 425. In particular, the focused particle beam is scanned over the object 425 using a scanning device 429. Then, an image of the scanned region of the object 425 can be generated by the detection signals, which are generated by the first analysis detector 419, and it can be displayed on a display unit. The display unit is for example a monitor 124 that is arranged at the monitoring unit 123.

The second analysis detector 428 is also connected to the monitoring unit 123. Detection signals of the second analysis detector 428 are supplied to the monitoring unit 123 and used to generate an image of the scanned region of the object 425 and to display it on a display unit. The display unit is for example the monitor 124 that is arranged at the monitoring unit 123.

A structural unit 125 of the particle beam apparatus 400 is arranged in the sample chamber 426. By way of example, the structural unit 125 is embodied in the form of a gas injection system, a micromanipulator, a further detector that is embodied to be movable and/or a charge compensation unit. The invention is not restricted to the aforementioned structural units. Rather, each structural unit of the particle beam apparatus 400 is utilizable for the invention.

Arranged at the sample chamber 426 is an imaging device 500, which will be discussed in more detail further below. The imaging device 500 is connected to the monitoring unit 123, which has the monitor 124. The monitoring unit 123 processes detection signals of the imaging device 500 and displays them in the form of images on the monitor 124. This will be discussed in more detail further below.

Figure 4:
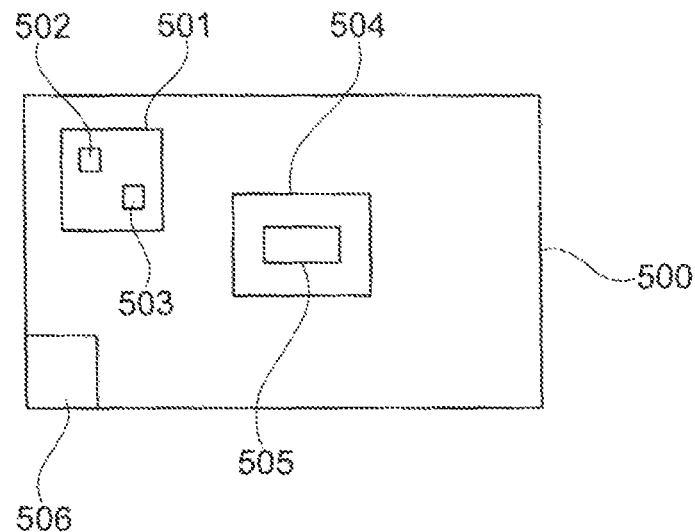
FIG. 4 shows a schematic illustration of a first exemplary embodiment of an imaging device for a particle beam apparatus.

FIG. 4 shows a first exemplary embodiment of the imaging device 500, which is arranged, for example, in one of the above-described particle beam apparatuses, specifically the SEM 100, the combination apparatus 200 and the particle beam apparatus 400.

The SEM 100, the combination apparatus 200 and the particle beam apparatus 400 together will also be referred to as particle beam apparatuses 100, 200 and 400 in the following text.

The imaging device 500 has an illumination unit 501. The illumination unit 501 illuminates the object 114 or 425 and/or the structural unit 125 with illumination light. In a first switching state of the illumination unit 501, the illumination light comprises only light of a first spectral range. By way of example, the illumination light comprises only a specific wavelength of the first spectral range. Alternatively, provision is made, for example, for the illumination light to be a superposition of a first light having a first wavelength and a second light having a second wavelength, with the first wavelength and the second wavelength being in the first spectral range. In a second switching state of the illumination unit 501, the illumination light comprises only light of a second spectral range. By way of example, the illumination light comprises only a specific wavelength of the second spectral range. Alternatively, provision is made, for example, for the illumination light to be a superposition of a third light having a third wavelength and a fourth light having a fourth wavelength, with the third wavelength and the fourth wavelength being in the second spectral range.

In an embodiment, provision is made, for example, for the first spectral range and the second spectral range to overlap to a minor extent, with an overlap range being less than 20 nm, for example. In that embodiment, provision is then made, for example, for the light of the first spectral range to have a proportion of less than 10% or less than 5% or less than 1% of the wavelengths from the overlap range. In that embodiment, provision is furthermore made, for example, for the light of the second spectral range to have a proportion of less than 10% or less than 5% or less than 1% of the wavelengths from the overlap range. In a further embodiment, provision is made for the first spectral range and the second spectral range to differ. The first spectral range and the second spectral range in this case have no shared intersection.

To generate light of the first spectral range, the illumination unit 501 has a first light-emitting unit 502. The first light-emitting unit 502 is provided with a first filter unit (not depicted), which is configured such that light that has no wavelength of the first spectral range is filtered out of the light generated by the first light-emitting unit 502. Provision is alternatively made for the first light-emitting unit 502 to generate only light of the first spectral range. By way of example, the first spectral range comprises the wavelength range from 380 nm to 780 nm, including the range boundaries.

In the exemplary embodiment of the imaging device 500 illustrated in FIG. 4, the first light-emitting unit 502 is embodied as an LED that emits white light. By way of example, this is an LED operating on the principle of luminescence wavelength conversion. In this principle, emitted blue radiation components of the LED are used to be partially converted into yellow light using a phosphor admixture. The generated spectra in sum consequently give white light.

The illumination unit 501 of the imaging device 500 also has a second light-emitting unit 503 for generating light of a second spectral range. The second light-emitting unit 503 is provided with a second filter unit (not depicted), which is configured such that light that has no wavelength of the second spectral range is filtered out of the light generated by the second light-emitting unit 503. Provision is alternatively made for the second light-emitting unit 503 to generate only light of the second spectral range. By way of example, the second spectral range is in the range from 780 nm to 3 μm, including the range boundaries. The second light-emitting unit 503 is embodied for example in the form of an infrared LED that emits light in the near infrared range. By way of example, the infrared LED emits infrared light that has a wavelength of 950 nm. It is explicitly noted that the invention is not limited to this wavelength. Rather, any wavelength that is suitable for performing the invention can be used for the light of the second spectral range.

As already mentioned above, the illumination unit 501 has a first switching state and a second switching state. Said switching states are controlled using a control unit 506 of the imaging device 500. In other words, the control unit 506 switches the illumination unit 501 into the first switching state or into the second switching state.

The imaging device 500 in accordance with FIG. 4 has a camera unit 504. The camera unit 504 serves for recording images of the object 114 or 425 and/or of the structural unit 125. To this end, the camera unit 504 is embodied having a detection unit 505. The detection unit 505 is, for example, a CCD or a CMOS. The detection unit 505 has a detector sensitivity. Said detector sensitivity is configured both for the light of the first spectral range in the first switching state of the illumination unit 501 and also for the light of the second spectral range in the second switching state of the illumination unit 501. In other words, the detection unit 505 of the camera unit 504 detects both the light of the first spectral range and the light of the second spectral range.

Figure 5:
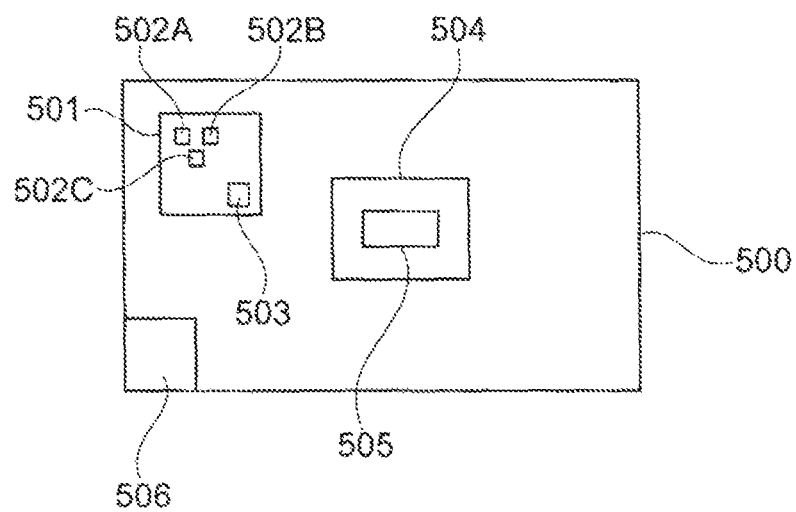
FIG. 5 shows a schematic illustration of a second exemplary embodiment of an imaging device for a particle beam apparatus.

FIG. 5 shows a second exemplary embodiment of the imaging device 500, which is arranged, for example, in one of the particle beam apparatuses 100, 200 and 400. The second exemplary embodiment of the imaging device 500 in accordance with FIG. 5 is based on the exemplary embodiment of the imaging device 500 in accordance with FIG. 4. Identical component parts are provided with identical reference signs. Therefore, reference is made to the explanations given above, which also apply to the second exemplary embodiment of the imaging device 500. In contrast to the first exemplary embodiment of the imaging device 500 in accordance with FIG. 4, the second exemplary embodiment of the imaging device 500 in accordance with FIG. 5 has a somewhat different illumination unit 501. The illumination unit 501 is also provided for illuminating the object 114 or 425 and/or the structural unit 125 with illumination light in the second exemplary embodiment. In the first switching state of the illumination unit 501, the illumination light comprises only light of the first spectral range. In the second switching state, the illumination light comprises only light of the second spectral range. To generate light of the first spectral range, the first light-emitting unit 502 has a plurality of LEDs, specifically a first LED 502A, a second LED 502B and a third LED 502C. The first LED 502A emits red light. The second LED 502B, by contrast, emits green light. The third LED 502C in turn emits blue light. By mixing the red, green and blue light, light is generated that is perceived as white light.

Figure 6:
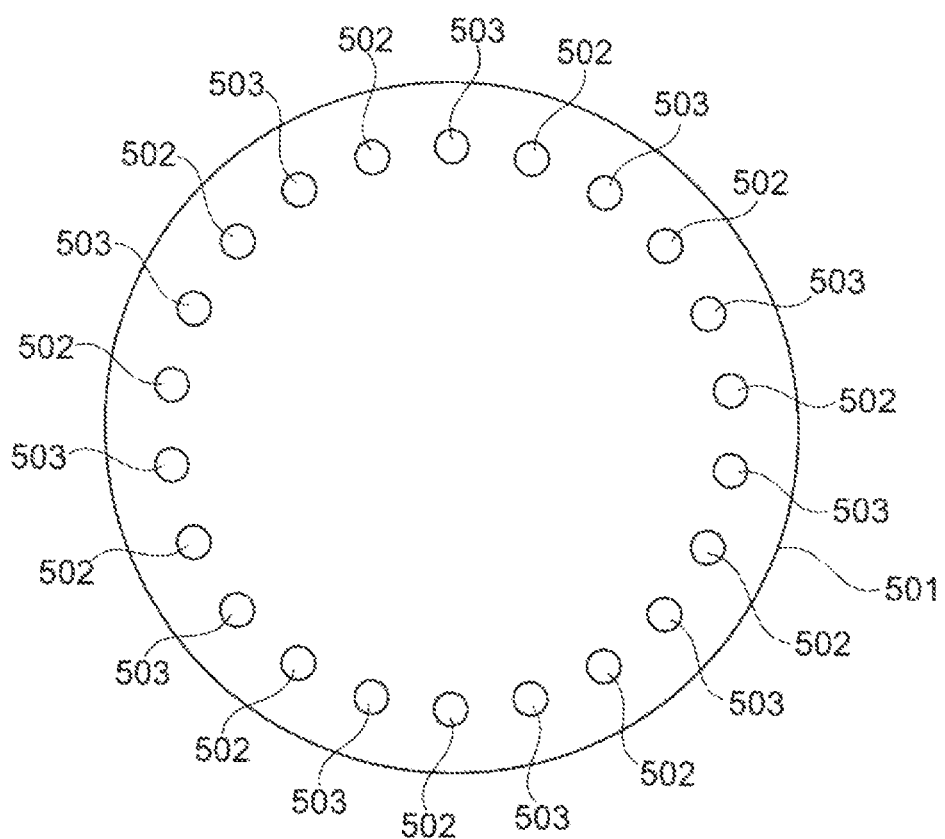
FIG. 6 shows an exemplary embodiment of an illumination unit.

FIG. 6 shows a further exemplary embodiment of the illumination unit 501. The exemplary embodiment of the illumination unit 501 in accordance with FIG. 6 is based on the exemplary embodiment of the illumination unit 501 in accordance with FIG. 4. Identical component parts are provided with identical reference signs. Therefore, reference is made to the explanations given above, which also apply to the exemplary embodiment of the illumination unit 501 in accordance with FIG. 6. In contrast to the exemplary embodiment of the illumination unit 501 in accordance with FIG. 4, the further exemplary embodiment of the illumination unit 501 in accordance with FIG. 6 has numerous first light-emitting units 502 and second light-emitting units 503, which are arranged annularly in alternating fashion at the illumination unit 501. The first light-emitting units 502 and the second light-emitting units 503 have the same functions, as have already been explained further above.

Figure 7:
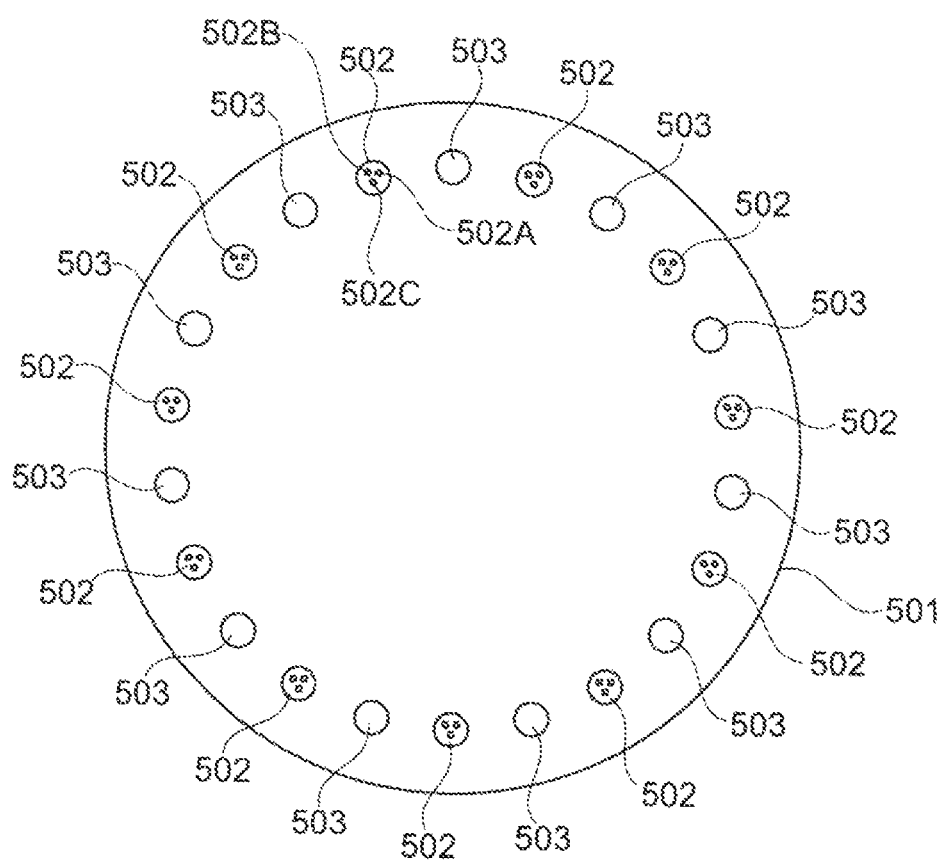
FIG. 7 shows a further exemplary embodiment of an illumination unit.

FIG. 7 shows a yet further exemplary embodiment of the illumination unit 501. This further exemplary embodiment of the illumination unit 501 in accordance with FIG. 7 is based on the exemplary embodiment of the illumination unit 501 in accordance with FIG. 5. Identical component parts are provided with identical reference signs. Reference is made to the explanations given above, which also apply to the further exemplary embodiment of the illumination unit 501 in accordance with FIG. 7. In contrast to the exemplary embodiment of the illumination unit 501 in accordance with FIG. 5, the further exemplary embodiment of the illumination unit 501 in accordance with FIG. 7 has numerous first light-emitting units 502 and second light-emitting units 503, which are arranged annularly in alternating fashion at the illumination unit 501. Each of the light-emitting units 502 has a plurality of LEDs, specifically a first LED 502A, a second LED 502B and a third LED 502C. The first LED 502A, the second LED 502B, the third LED 502C and the second light-emitting unit 503 have the same functions as have already been explained further above. They also apply to this exemplary embodiment.

The exemplary embodiments in accordance with FIGS. 6 and 7 have the advantage that driving the first light-emitting units 502 and the second light-emitting units 503 can be effected such that illumination of sectors within the sample chambers 120, 201 or 426 can be performed. In other words, the emission direction of the light of the first spectral range and the light of the second spectral range is freely selectable. As a result, it may be possible to reduce reflections inside the sample chamber 120, 201 or 426, which impair the function of the detectors 116, 117, 121, 419 or 428.

Figure 8:
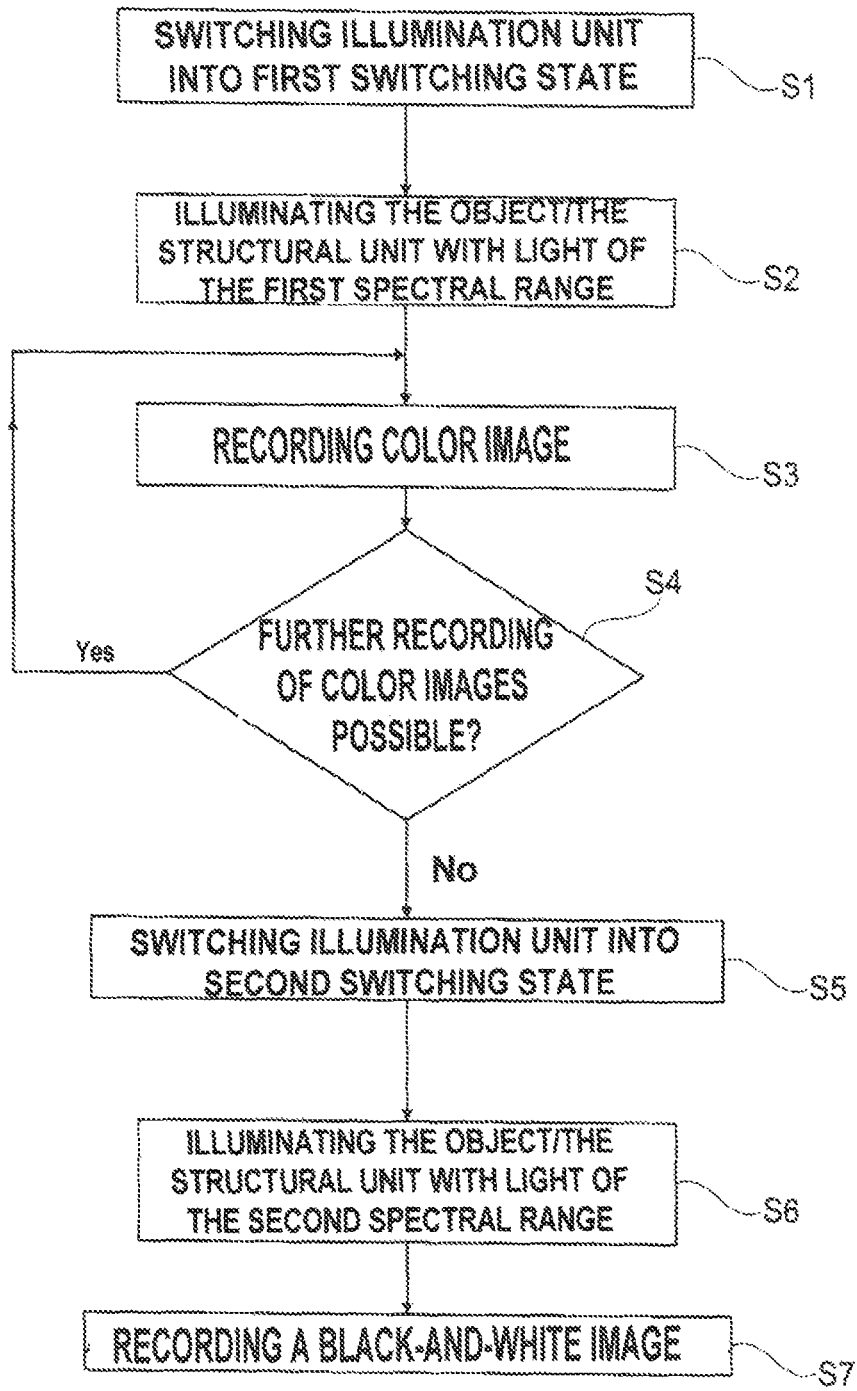
FIG. 8 shows a method for operating a particle beam apparatus having an imaging device.

FIG. 8 illustrates a method for operating the above-described particle beam apparatuses 100, 200 and 400. In a method step S1, the illumination unit 501 is switched into the first switching state using the control unit 506. In the first switching state, the illumination unit 501 generates only light of the first spectral range in the form of white light. In a method step S2, the object 114 or 425 and/or the structural unit 125 is then illuminated with the light of the first spectral range. In method step S3, a color image or a plurality of color images is/are then recorded using the camera unit 504 and displayed on the monitor 124.

In method step S4, a check is performed as to whether a further recording and generation of color images are possible. The further recording and generation of color images can be possible in a plurality of cases. For example, they are possible if the object 114 or 425 is not imaged with a particle beam of the particle beam apparatus 100, 200 or 400. In this case, the illumination of the object 114 or 425 and/or of the structural unit 125 with light of the first spectral range in the form of white light is easily possible, since the detectors 116, 117, 121, 419 and 428 of the particle beam apparatuses 100, 200 and 400 are not used. In this case, no disturbance can accordingly occur in the detectors 116, 117, 121, 419 and 428 of the particle beam apparatuses 100, 200 and 400. A further recording and generation of color images are also possible if the detectors 116, 117, 119, 121, 419 and 428 of the particle beam apparatuses 100, 200 and 400 are not sensitive for light of the first spectral range or are not in operation. If they are not sensitive, simultaneous recording of color images using the imaging device 500 and imaging of the object 114 or 425 using the particle beam that is incident on the object 114 or 425 and the detectors 116, 117, 119, 121, 419 and 428 of the particle beam apparatuses 100, 200 and 400 are possible. A further recording and generation of color images are also possible in particular if the detectors are arranged in the particle beam apparatuses 100, 200 and 400 such that no light or only very little light of the first spectral range can be incident on said detectors. For example, these are the second detector 117 of the SEM 100 or the second analysis detector 428 of the particle beam apparatus 400.

In method step S4, it is possible to perform an additional check as to whether a further recording and generation of color images are desired but not possible owing to a possible disturbance of the detectors 116, 117, 119, 121, 419 and 428 by light of the first spectral range. In that case, provision is made, for example, to switch off the detector 116, 117, 119, 121, 419 and 428 in the first switching state. Provision is additionally or alternatively made for the detectors 116, 117, 119, 121, 419 and 428 to be moved into a position such that, in the first switching state, no light of the first spectral range is incident on the detectors 116, 117, 119, 121, 419 and 428. Provision is in turn additionally or alternatively made for the detectors 116, 117, 119, 121, 419 and 428 to be moved into a position such that, in the first switching state, only a minimum intensity of the light of the first spectral range is incident on the detectors 116, 117, 119, 121, 419 and 428. In all previously mentioned cases, it is then possible to furthermore generate color images of the object 114 or 425 and/or of the structural unit 125 with light of the first spectral range.

If a further recording of color images is possible, method step S3 is repeated. However, if a determination is made in method step S4 that a further recording of color images is not possible—for example because a simultaneous imaging of the object 114 or 425 with the particle beam of the particle beam apparatuses 100, 200 and 400 is not possible and/or because the detectors 116, 117, 119, 121, 419 and 428 of the particle beam apparatuses 100, 200 and 400 are disturbed by light of the first spectral range—the control unit 506 in method step S5 switches the illumination unit 501 into the second switching state. In the second switching state, the object 114 or 425 and/or the structural unit 125 is then illuminated with light of the second spectral range (method step S6). As mentioned above, the light of the second spectral range is infrared light. The camera unit 504 is now used to record black-and-white images of the object 114 or 425 and/or of the structural unit 125 (method step S7) and to display them on the monitor 124.

Figure 9:
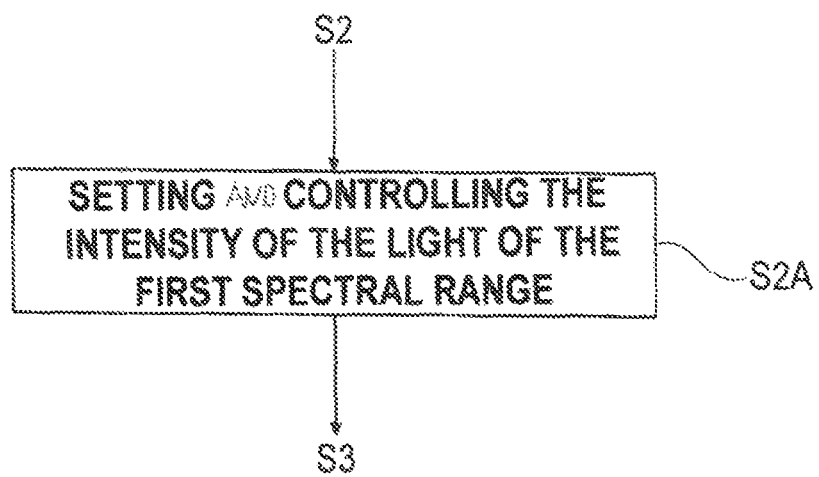
FIG. 9 shows a further method step of a further exemplary embodiment of the method of FIG. 8.
Figure 10:
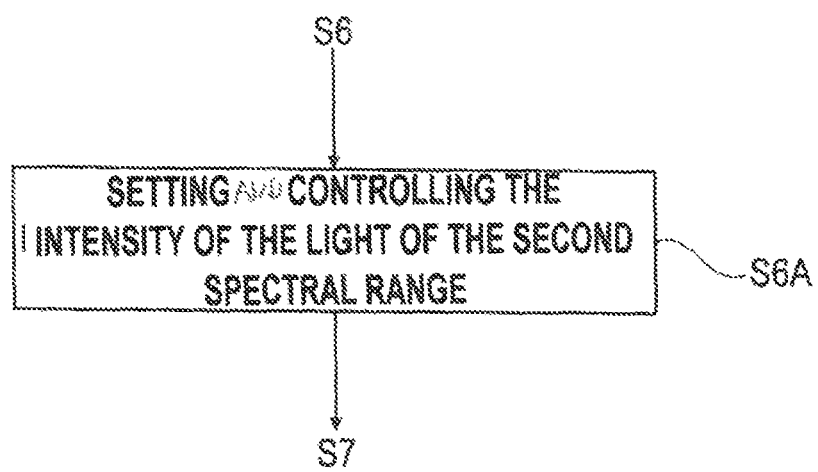
FIG. 10 shows a further method step of a yet further exemplary embodiment of the method of FIG. 8.

FIG. 9 shows a further method step S2A, which is performed in a further exemplary embodiment of the method in accordance with FIG. 8 between the method steps S2 and S3. In method step S2A, the intensity of the light of the first spectral range is set and controlled by the control unit 506. FIG. 10 shows a further method step S6A, which is performed in a yet further exemplary embodiment of the method in accordance with FIG. 8 between the method steps S6 and S7. In method step S6A, the intensity of the light of the second spectral range is set and controlled by the control unit 506. The exemplary embodiments of FIGS. 9 and 10 ensure that disturbing influences on a detector, such as the detectors 116, 117, 119, 121, 419 and 428, are minimized and at the same time good imaging of the object 114 or 425 and/or of the structural unit 125 with the imaging device 500 is ensured.

The system described herein ensures that imaging of the object 114 or 425 and/or of the structural unit 125 with the camera unit 504 is possible in every operating state of the particle beam apparatus 100, 200 or 400. Recording of color images using the camera unit 504 is ensured, for example, until simultaneous recording of color images and imaging of the object 114 or 425 with the particle beam of the particle beam apparatus 100, 200 or 400 are no longer possible. Objects marked or configured in color are easily identifiable by way of the color images generated. If, for example, simultaneous recording of color images and imaging of the object 114 or 425 or of the structural unit 125 with the particle beam of the particle beam apparatus 100, 200 or 400 is no longer possible, the control unit 506 switches the illumination unit 501 into the second switching state. In the second switching state, light of the second spectral range, specifically infrared light, is used for illuminating and imaging the object 114 or 425 and/or the structural unit 125. Black-and-white images of the object 114 or 425 and/or of the structural unit 125 are then generated. The light of the second spectral range is configured such that simultaneous recording of an image of the object 114 or 425 and/or of the structural unit 125 using the camera unit 504 and imaging of the object 114 or 425 by detecting interaction particles using the detectors 116, 117, 119, 121, 419 and 428 is possible. As a result, it is also always ensured that the object 114 or 425 and/or the structural unit 125 is/are observable in every operating state of the particle beam apparatus 100, 200 or 400 and, for example, it is possible to set, in a controlled fashion, the position of the object 114 or 425 using the sample stage 122 and 424 and/or the position of the structural unit 125.

In a particle beam apparatus having an imaging device according to the system described herein, the first spectral range can comprise the entire visible spectrum with the entire wavelength range from 400 nm to 700 nm, or a significant portion of the visible spectrum, at least with the wavelength range from 450 nm to 650 nm. The second spectral range can then be selected such that at least one detector, which is arranged in the sample chamber of the particle beam apparatus or in the vicinity of the sample chamber in the beam tube of the particle beam apparatus and which serves for detecting interaction products of the particle beam with the object, is sensitive for light in the first spectral range, but is non-sensitive for light in the second spectral range. If a plurality of detectors for detecting interaction products of the particle beam with the object are arranged in the sample chamber or in the vicinity of the sample chamber in the beam tube of the particle beam apparatus, all these detectors should be non-sensitive for light of the second spectral range. The control unit can here be embodied such that it preferably operates the illumination unit of the imaging device in the first switching state, in which the illumination light comprises the first spectral range, and switches the illumination unit into the second switching state only if at least one detector which is arranged in the sample chamber of the particle beam apparatus or in the vicinity of the sample chamber in the beam tube of the particle beam apparatus and which serves for detecting interaction products of the particle beam with the object and which is sensitive for light in the first spectral range is in operation. In this way, the imaging device can be used to generate and provide preferably color images of the interior of the sample chamber, except exactly in those cases in which the recording of color images would result in disturbing detection signals; but even if detectors that are sensitive for the illumination light necessary for recording color images are in operation, it is still possible to provide black-and-white images of the interior of the sample chamber.

In a further embodiment, the control unit of the imaging device can also have a third switching state, in which the illumination unit is completely switched off, i.e. no illumination light at all is made available by the illumination unit. This third switching state is set by the control unit only if all the detectors for detecting interaction products of the particle beam with the object which are arranged in the sample chamber or in the vicinity of the sample chamber in the beam tube of the particle beam apparatus and which are in operation are sensitive at least for light in the first spectral range or for light in the second spectral range, or if the user manually sets this third switching state. In this third switching state, it is not then possible for the imaging device to provide images of the interior of the sample chamber, but it is ensured that the image signals obtained using the detectors are not disturbed by illumination light of the imaging device.

The features of the invention disclosed in the present description, in the drawings and in the claims may be essential for the realization of the invention in the various embodiments thereof, both individually and in arbitrary combinations. The invention is not restricted to the described embodiments. It may be varied within the scope of the claims, taking into account the knowledge of the relevant person skilled in the art.

What is claimed is:

1. A particle beam apparatus for analyzing and/or processing an object, having:
    at least one beam generator for generating a particle beam comprising charged primary particles;
    at least one objective lens for focusing the particle beam onto the object, wherein interaction particles and/or interaction radiation arise/arises during an interaction of the particle beam with the object;
    at least one detector for detecting the interaction particles and/or interaction radiation, wherein the at least one detector is sensitive to light of a first spectral range and is non-sensitive to light in a second spectral range; and
    at least one imaging device for imaging the object and/or for imaging a structural unit of the particle beam apparatus, the at least one imaging device having:
        at least one illumination unit with a first switching state and a second switching state for illuminating the object and/or for illuminating the structural unit with illumination light, wherein, in the first switching state, the illumination light includes only light of the first spectral range and wherein, in the second switching state, the illumination light includes only light of the second spectral range,
        at least one control unit for switching the illumination unit into the first switching state or into the second switching state, wherein the control unit operates the illumination unit of the imaging device in the first switching state and switches the illumination unit into the second switching state only if the at least one detector is: (i) in operation, and (ii) in a position in which the at least one detector detects light of the first spectral range in the first switching state, and
        at least one camera unit for imaging the object and/or for imaging the structural unit with light of the first spectral range in the first switching state of the illumination unit or with light of the second spectral range in the second switching state of the illumination unit.

2. The particle beam apparatus as claimed in claim 1, wherein the imaging device has at least one of the following features:
    (i) the first spectral range comprises only the wavelength range of visible light;
    (ii) the first spectral range comprises only light of a wavelength range of 380 nm to 780 nm;
    (iii) the first spectral range comprises only white light.

3. The particle beam apparatus as claimed in claim 1, wherein the imaging device has at least one of the following features:
    (i) the second spectral range comprises only the wavelength range of infrared light;
    (ii) the second spectral range comprises only the wavelength range of near infrared light;
    (iii) the second spectral range comprises only light of a wavelength range of 780 nm to 3.0 µm.

4. The particle beam apparatus as claimed in claim 1, wherein the imaging device has at least one of the following features:
    (i) at least one first light-emitting unit for generating the light of the first spectral range;
    (ii) at least one first light-emitting unit for generating the light of the first spectral range, wherein the first light-emitting unit has a first filter unit;
    (iii) at least one first light-emitting unit for generating the light of the first spectral range, wherein the first light-emitting unit has at least one LED;
    (iv) at least one first light-emitting unit for generating the light of the first spectral range, wherein the first light-emitting unit has at least one first LED and/or at least one second LED and/or at least one third LED;
    (v) at least one second light-emitting unit for generating the light of the second spectral range;
    (vi) at least one second light-emitting unit for generating the light of the second spectral range, wherein the second light-emitting unit has a second filter unit;
    (vii) at least one second light-emitting unit for generating the light of the second spectral range, wherein the light-emitting unit has at least one LED.

5. The particle beam apparatus as claimed in claim 1, wherein
    the camera unit has at least one detection unit having a detector sensitivity, and wherein
    the detector sensitivity is configured both for the light of the first spectral range in the first switching state of the illumination unit and also for the light of the second spectral range in the second switching state of the illumination unit.

6. The particle beam apparatus as claimed in claim 1, wherein the camera unit has at least one CCD or one CMOS.

7. The particle beam apparatus as claimed in claim 1, wherein the control unit is embodied as an intensity control unit for setting and/or controlling the intensity of the light of the first spectral range and/or of the light of the second spectral range.

8. The particle beam apparatus as claimed in claim 1, wherein
    the particle beam apparatus has a sample chamber, and wherein
    the imaging device is arranged at the sample chamber and/or in the sample chamber.

9. The particle beam apparatus as claimed in claim 1, wherein the particle beam apparatus has at least one mirror corrector for correcting chromatic and/or spherical aberration.

10. The particle beam apparatus as claimed claim 1, wherein the particle beam apparatus is designed as an electron beam apparatus and/or as an ion beam apparatus.

11. The particle beam apparatus as claimed in claim 1, wherein the beam generator for generating a particle beam comprising charged primary particles is designed as a first beam generator for generating a first particle beam comprising first charged primary particles and the objective lens is designed as a first objective lens for focusing the first particle beam, and wherein the particle beam apparatus furthermore has:
    at least one second beam generator for generating a second particle beam comprising second charged primary particles, and
    at least one second objective lens for focusing the second particle beam onto the object.

12. The particle beam apparatus as claimed in claim 1, wherein the structural unit of the particle beam apparatus is embodied as a gas injection system, a micromanipulator, a detector that is embodied to be movable and/or as a charge compensation unit.

13. The particle beam apparatus as claimed in claim 8, wherein the structural unit of the particle beam apparatus is arranged in the sample chamber.

14. A method for operating a particle beam apparatus as claimed in claim 1, wherein:
    the control unit switches the illumination unit into the first switching state or into the second switching state, including operating the illumination unit of the imaging device in the first switching state and switching the illumination unit into the second switching state only if the at least one detector is: (i) in operation, and (ii) in a position in which the at least one detector detects light of the first spectral range in the first switching state, and
    in the first switching state, the object and/or the structural unit is imaged with the light of the first spectral range using the camera unit and wherein, in the second switching state, the object and/or the structural unit is imaged with the light of the second spectral range using the camera unit.

15. The method as claimed in claim 14, wherein, in the first switching state, the particle beam is guided away from the object or is switched off.

16. The method as claimed in claim 14, wherein the intensity of the light of the first spectral range and/or the intensity of the light of the second spectral range is/are set using the control unit.

17. The method as claimed in claim 14, having at least one of the following steps:
    switching off the detector in the first switching state;
    moving the detector into a position such that, in the first switching state, no light of the first spectral range is incident on the detector;
    moving the detector into a position such that, in the first switching state, only a minimum intensity of the light of the first spectral range is incident on the detector.

* * * * *